United States Patent [19]

Muraishi

[11] Patent Number: 5,102,624
[45] Date of Patent: Apr. 7, 1992

[54] CHEMICAL ANALYSIS APPARATUS
[75] Inventor: Katsuaki Muraishi, Kanagawa, Japan
[73] Assignee: Fuji Photo Film Co., Ltd., Kanagawa, Japan
[21] Appl. No.: 95,376
[22] Filed: Sep. 3, 1987
[30] Foreign Application Priority Data Sep. 3, 1986 [JP] Japan .................. 61-207047

[51] Int. Cl.$^5$ .......................... G01N 35/00
[52] U.S. Cl. ......................... 422/64; 422/66; 422/68.1
[58] Field of Search ............ 422/55, 63, 64, 65, 422/66, 68; 364/497, 498

[56] References Cited

U.S. PATENT DOCUMENTS

| | | |
|---|---|---|
| 4,190,420 | 2/1980 | Covington et al. ............ 422/63 |
| 4,296,069 | 10/1981 | Smith et al. ................. 422/65 |
| 4,302,420 | 11/1981 | Jakubowicz et al. ........... 422/65 |
| 4,313,735 | 2/1982 | Yamashita et al. ............ 422/65 |
| 4,430,299 | 2/1984 | Horne et al. ................. 422/66 |
| 4,512,952 | 4/1985 | Blanding et al. ............. 422/63 |
| 4,539,296 | 9/1985 | Manabe ....................... 436/164 |
| 4,568,519 | 2/1986 | Hamilton et al. ............. 422/62 |
| 4,584,275 | 4/1986 | Okano et al. ................. 422/65 |
| 4,720,463 | 1/1988 | Farber et al. ................ 422/65 |

FOREIGN PATENT DOCUMENTS 60-57259 3/1985 Japan .
2293161 12/1987 Japan ..................... 422/58

Primary Examiner—Robert J. Hill, Jr.
Attorney, Agent, or Firm—Sughrue, Mion, Zinn, Macpeak & Seas

[57] ABSTRACT

A chemical analysis apparatus comprises an incubator provided with a plurality of chambers disposed on the same circumference for each housing a chemical analysis slide, a sample application device disposed above the incubator at a predetermined position on the circuumference, and a probe disposed below the incubator at the predetermined position. A rotation system is provided for rotating the incubator to locate the chambers one after another at the predetermined position. A slide feeder is disposed outward or inward of the circumference to face the predetermined position, and a slide ejection unit is disposed on the side opposite to the slide feeder with the predetermined position intervening between the slide ejection unit and the slide feeder. The chemical analysis slide in each of the chambers is pushed out and ejected by feeding of a new chemical analysis into the chamber.

5 Claims, 2 Drawing Sheets

CHEMICAL ANALYSIS APPARATUS

BACKGROUND OF THE INVENTION

1. Field of the Invention

This invention relates to a chemical analysis apparatus provided with an incubator having a plurality of chambers on the same circumference.

2. Description of the Prior Art

In general, it is often desired to investigate whether a specific constituent is or is not contained in a liquid sample such as blood or blood serum or to investigate the contents of specific constituents in the liquid sample. For this purpose, chemical analysis using a reaction reagent is carried out. The chemical analysis methods for liquid samples are classified into a dry method and a wet method. In the dry method, a sample solution is analyzed by use of a chemical analysis slide having a reagent layer impregnated with a predetermined reagent. Specifically, a measured amount of a sample solution is put on the reagent layer of the chemical analysis slide and is maintained at a predetermined temperature (i.e., incubated) for a predetermined time in an incubator to cause a color reaction, the chemical analysis slide is exposed to measuring light having a wavelength selected in advance in accordance with the combination of the sample constituent with a reagent contained in the reagent layer of the chemical analysis slide, and the optical density in terms of the light reflected by the chemical analysis slide is measured In this manner, quantitative analysis of the chemical analysis constituent or the like is carried out.

In medical organizations, research laboratories or the like in which many sample solutions are to be analyzed, it is desired that the analysis be carried out automatically and continuously. To satisfy this need, there have been proposed various chemical analysis apparatuses for carrying out sample analysis automatically and continuously by use of the aforesaid chemical analysis slides.

For example, it has been proposed in Japanese Unexamined Patent Publication No. 60(1985)-57259 to constitute a chemical analysis apparatus so that a disk on which a plurality of chemical analysis slides are disposed in an equally spaced relation to each other on the same circumference is housed for a predetermined time in a pre-heating chamber of an incubator, the pre-heated disk is moved to a measurement chamber of the incubator and incubated therein, a necessary amount of a sample solution is applied by use of a pipette onto the chemical analysis slides while they are being incubated, and measurement of the optical density in terms of the reflected light is carried out by rotating the disk and closely contacting the respective chemical analysis slides one after another with a probe. After the measurement is finished for all of the chemical analysis slides, the disk is taken out of the measurement chamber, a disk on which chemical analysis slides without a sample solution applied thereon are disposed and which has been pre-heated in the pre-heating chamber is fed into the measurement chamber, and the aforesaid operations are repeated.

However, since it is necessary that sample analysis be carried out continuously and rationally as mentioned above, a need exists for a more automatic and rational method of sample analysis.

Particularly in the case where rate measurement is to be carried out after carrying out background measurement for each of a plurality of the chemical analysis slides by use of a single probe, besides irradiation of the measuring light for the background measurement and the rate measurement, it is necessary to carry out feeding of the chemical analysis slides into and ejection thereof from the chambers of the incubator, application of a sample solution or the like. A long time is required for the respective operations, and it is not always possible to carry out rate measurement of the respective chemical analysis slides at short intervals. Accordingly, a need exists for a chemical analysis apparatus which can perform the respective operations quickly and efficiently.

By the term "background measurement" as used herein is meant the measurement of the optical reflection density of the chemical analysis slide without a sample solution applied thereon, which is carried out for discriminating whether or not the chemical analysis slide is acceptable for rate measurement or for compensation of the optical reflection density measured after a color reaction is effected on the chemical analysis slide.

By the term "rate measurement" as used herein is meant the measurement of a change rate of the optical reflection density by measuring the optical reflection density a plurality of times for a single chemical analysis slide at short time intervals within the range of, for example, 5 to 10 seconds. When the time interval is long, the accuracy of the rate measurement is deteriorated.

SUMMARY OF THE INVENTION

The primary object of the present invention is to provide a chemical analysis apparatus which makes it possible to carry out the aforesaid operation efficiently.

Another object of the present invention is to provide a chemical analysis apparatus which enables efficient and quick chemical analysis.

The present invention provides a chemical analysis apparatus comprising:

i) an incubator provided with a plurality of chambers disposed on the same circumference for each housing a chemical analysis slide, ii) a sample application means disposed above said incubator at a predetermined position on said circumference, and a probe disposed below said incubator at said predetermined position, iii) a rotation means for rotating said incubator to locate said chambers one after another at said predetermined position, and iv) a slide feed means disposed outward or inward of said circumference to face said predetermined position, and a slide ejection unit disposed on the side opposite to said slide feed means with said predetermined position intervening between said slide ejection unit and said slide feed means, wherein said chemical analysis slide in each of said chambers is pushed out and ejected by feeding of a new chemical analysis slide into said chamber.

With the chemical analysis apparatus in accordance with the present invention, a rotatable incubator having chambers formed on the same circumference is provided, a sample application means and a probe are disposed at a predetermined position on the circumference and the slide feed means and the slide ejection unit are disposed on a straight line which includes said predetermined position. Therefore, feeding of a chemical analysis slide into each of the chambers, the background measurement, application of a sample solution, and ejection of the chemical analysis slide can be carried out continuously and very quickly as a series of operations on the same straight line. As a result, for example, rate measurements of a plurality of the chemical analysis slides in the respective chambers can be carried out simultaneously and continuously at very short time intervals.

Thus, the chemical analysis apparatus in accordance with the present invention is very advantageous for achieving accurate, efficient and smooth analysis of many sample solutions.

DESCRIPTION OF THE PREFERRED EMBODIMENTS

The present invention will hereinbelow be described in further detail with reference to the accompanying drawings.

Figure 1:
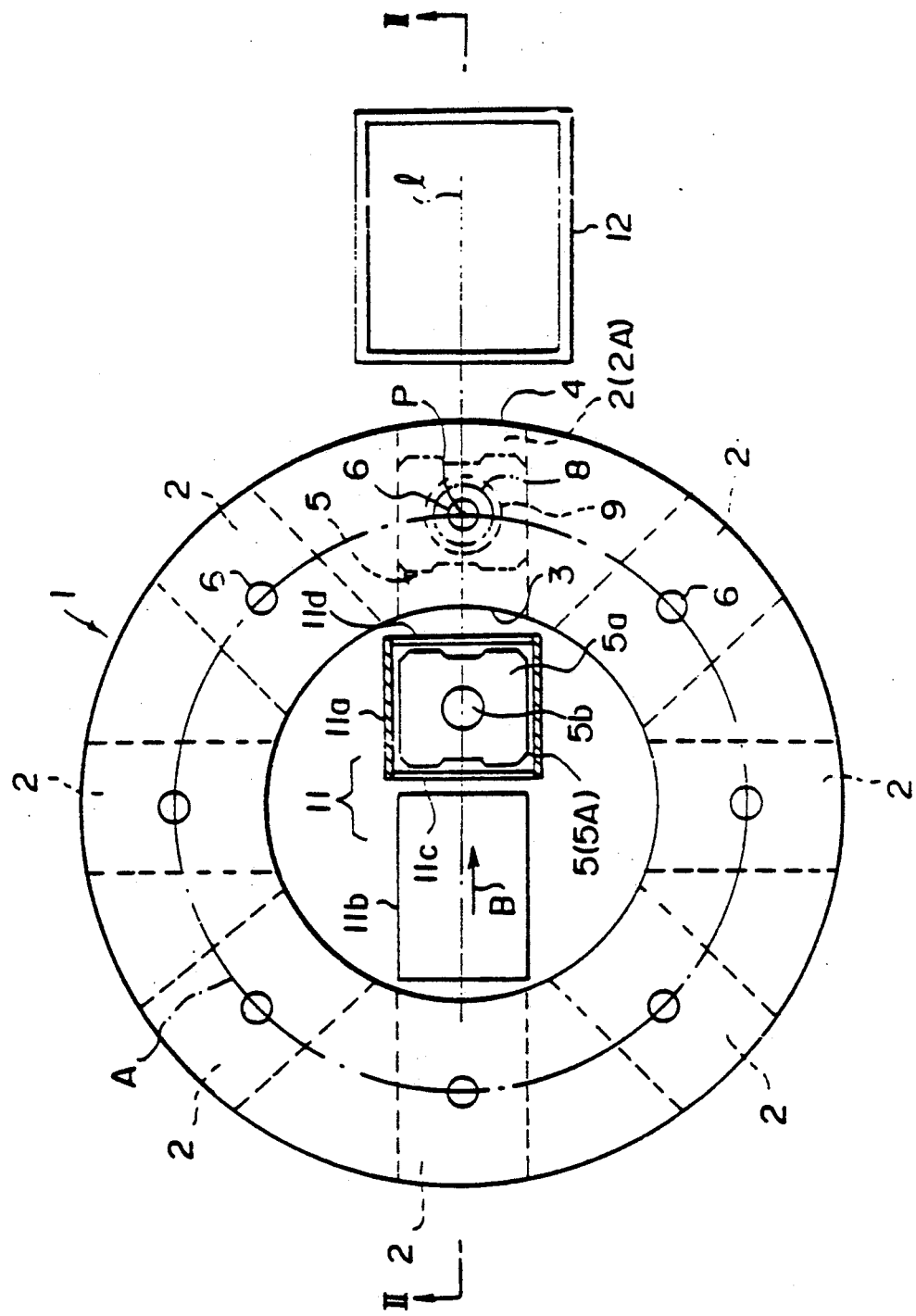
FIG. 1 is a schematic plan view showing an embodiment of the chemical analysis apparatus in accordance with the present invention.
Figure 2:
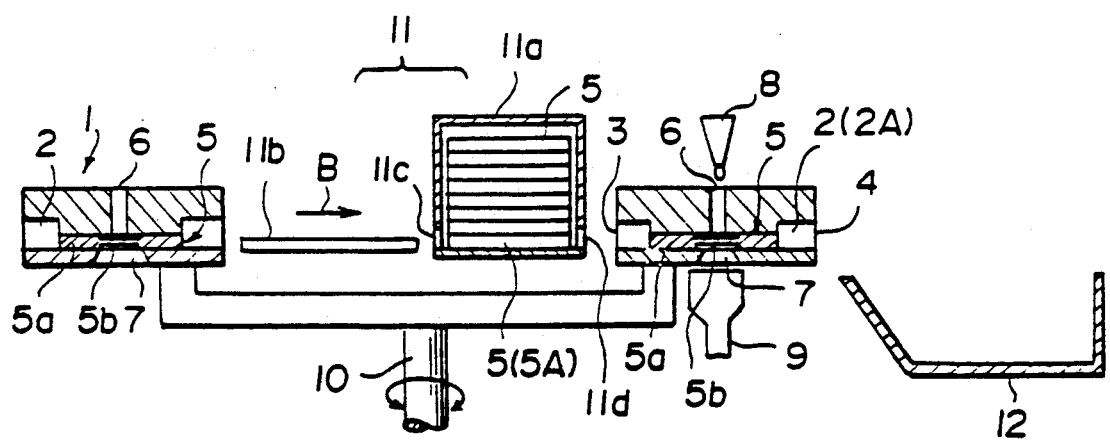
FIG. 2 is a sectional view taken along line II—II in FIG. 1.

As shown in FIGS. 1 and 2, an embodiment of the chemical analysis apparatus is provided with an incubator 1 shaped in a doughnut shape. The incubator 1 is provided therein with eight chambers 2, 2, ..., formed in an equally spaced relation to each other on the same circumference A for each housing a chemical analysis slide 5. The incubator 1 is also provided with a temperature sensor (not shown) and a heater (not shown) so that the chemical analysis slides 5, 5, ... housed in the chambers 2, 2, ... can be maintained (incubated) at predetermined temperatures.

Each of the chambers 2, 2, ... is provided with a feed-in opening 3 formed on the inner circumference side of the incubator 1, and an ejection opening 4 formed on the outer circumference side of the incubator 1, and can house a single chemical analysis slide 5 therein.

Each of the chemical analysis slides 5, 5, ... comprises a frame 5a having a circular hole for application of a sample solution, and a dry type multi-layer film 5b disposed in the frame 5a and composed of a supporting material, a reagent layer, and a spreading layer, which are stacked in this sequence. A predetermined amount of the sample solution (i.e., the substance to be measured) such as urine or blood is fed onto the film 5b, and incubated to cause a color reaction.

A sample application opening or conduit 6 has an outer end, which opens at the upper surface of the incubator 1, and an inner end which opens at an upper portion of a corresponding one of the chambers 2, 2, .... Also, a measurement opening or conduit 7 is provided having an outer end, which opens at the lower surface of the incubator 1, and an inner end which opens at a lower portion of a corresponding one of the chambers 2, 2, .... The sample application opening 6 and the measurement opening 7 are formed to face the multi-layer film 5b of the chemical analysis slide 5 when the chemical analysis slide 5 is housed in each of the chambers 2, 2, ....

A sample application means 8 (e.g., a pipette) is disposed above the incubator 1 at a predetermined position P on the circumference A along with the chambers 2, 2, ... are located. The sample application means 8 applies the sample solution via the sample application opening 6 from above onto the multi-layer film 5b of the chemical analysis slide 5 housed in a chamber 2A located at the predetermined position P. Also, a probe 9 as an optical measurement means is disposed below the incubator 1 at the predetermined position P. The probe 9 emits measuring light via the measurement opening 7 to the multi-layer film 5b of the chemical analysis slide 5 housed in the chamber 2A located at the predetermined position P, and measures the optical density in terms of the light reflected by the multilayer film 5b. When necessary, a light-permeable member formed of glass or the like is fitted to the measurement opening 7.

The doughnut-shaped incubator 1 is constituted rotatably. Specifically, the chambers 2, 2, ... are supported horizontally by a rotation means 10 so that they can be located at the predetermined position P one after another through rotation, and are rotated at intervals of predetermined angles (at 45° intervals in this embodiment) when necessary.

Also, a slide feed means 11 for feeding the chemical analysis slide 5 into the chamber 2A and a slide ejection unit 12 for ejecting the chemical analysis slide 5 after optical measurement are disposed on a straight line 1 connecting the predetermined position P with the center of the circumference A along which the chambers 2, 2, ... are located.

The slide feed means 11 will be described in further detail below. A feed unit 11a capable of stacking therein a plurality of the chemical analysis slides 5, 5, ... (eight chemical analysis slides in this embodiment) is disposed on the chamber 2A side of the center portion of the doughnut-shaped incubator 1. A pushing lever 11b for pushing the lowest chemical analysis slide 5A among the chemical analysis slides 5, 5, ... in the feed unit 11a into the chamber 2A is on the side opposite to the chamber 2A with respect to the feed unit 11a. The pushing lever 11b is moved in the direction as indicated by the arrow B, and is inserted into the feed unit 11a via a lever inlet opening 11c opened in a shape approximately corresponding to a side face of the chemical analysis slide 5 and formed at the lower portion of the side wall of the feed unit 11a located normal to the straight line 1. In this manner, the pushing lever 11b pushes the chemical analysis slide 5A in the direction as indicated by the arrow B, and ejects it through a slide outlet 11d.

The procedure of the optical measurement in the aforesaid embodiment will be described hereinbelow. In the aforesaid embodiment, a plurality of the chemical analysis slides 5, 5, ... without the sample solution applied thereon are housed in the feed unit 11a. The pushing lever 11b is moved in the direction as indicated by the arrow B to push the lowest chemical analysis slide 5A in the direction as indicated by the arrow B out of the feed unit 11a, and to feed it up to a predetermined position as shown in the chamber 2A located at the predetermined position P In this manner, a new chemical analysis slide 5A not having the sample solution applied thereon is fed by the pushing lever 11b into the chamber 2A and, at the same time, the chemical analysis slide 5 which has been housed up to then in the chamber 2A and for which the optical measurement has already been finished is pushed out of the chamber 2A by the feeding of the new chemical analysis slide 5A into the chamber 2A Specifically, the chemical analysis slide 5 for which the optical measurement has already been finished is pushed out in the direction as indicated by the arrow B by the new chemical analysis slide 5A fed in the direction as indicated by the arrow B, and is ejected into a slide ejection unit 12 composed of a measured slide receiving vessel. After feeding the new chemical analysis slide 5A into the chamber 2A, the pushing lever 11b is moved reversely to the direction B and returned to the original position.

Immediately upon the new chemical analysis slide 5A being housed in the chamber 2A, the background measurement, i.e., the measurement of the optical reflection density of the chemical analysis slide 5A without the sample solution applied thereon, is carried out via the measurement opening 7 by the probe 9 disposed below the chamber 2A. After the background measurement is finished, the sample solution is immediately applied onto the multi-layer film 5b of the chemical analysis slide 5A via the sample application opening 6 by the sample application means 8 disposed above the chamber 2A.

After slide feeding, slide ejection, background measurement, and sample application at the chamber 2A are finished in the manner as mentioned above, the incubator 1 is rotated by the rotation means 10 at intervals of, for example, 45°, and rate measurement is carried out once for the chemical analysis slides 5, 5, . . . housed in the other chambers 2, 2, . . . and the chemical analysis slide 5A housed in the chamber 2A. When the rate measurement has been carried out a predetermined number of times for the chemical analysis slide 5 housed in any one of the chambers 2, 2, . . . , the chamber 2 housing said chemical analysis slide 5 is located at the predetermined position P. Then, feeding of a new chemical analysis slide 5 into the chamber 2 located at the predetermined position P, ejection of the chemical analysis slide 5 for which the rate measurement has been finished out of said chamber 2, background measurement for the new chemical analysis slide 5, and sample application thereto are carried out in the same manner as mentioned above. The incubator 1 is then rotated, and the rate measurement is repeated for the chemical analysis slides 5, 5, . . . housed in the chambers 2, 2, . . . .

In order efficiently to achieve the measurement of optical density in terms of the reflected light, it is necessary to carry out the measurement simultaneously and continuously for a plurality of the chemical analysis slides 5, 5, . . . in the chambers 2, 2, . . . . However, in the case of the rate measurement, for example, measurement is carried out many times at short time intervals of, for example, 10 seconds for a single chemical analysis slide 5. In order to carry out the rate measurement simultaneously and continuously for the chemical analysis slides 5, 5, . . . housed in the chambers 2, 2, . . . , it is necessary that the operations of ejection of the chemical analysis slide 5 for which the optical measurement has been finished out of a single chamber 2, feeding of a new chemical analysis slide 5 without the sample solution applied thereon into said chamber 2, background measurement of said new chemical analysis slide 5, and sample application to said new chemical analysis slide 5, and the rate measurement operation for measuring once the chemical analysis slide 5 in each of the chambers 2, 2, . . . be achieved within 10 seconds. For this purpose, slide feeding, slide ejection, sample application and background measurement must be carried out quickly and efficiently.

With the aforesaid embodiment, the incubator 1 having a plurality of the slide chambers 2, 2, . . . disposed along the circumference A is provided, and the sample application means 8 and the probe 9 are respectively disposed above and below the circumference A at the predetermined position P. Also, the slide feed means 11 and the slide ejection unit 12 are disposed in the direction intersecting with the circumference A, preferably on the straight line 1 in the radial direction, and the chemical analysis slide 5 for which the optical measurement has already been finished is ejected out of the chamber 2 automatically by the pushing of the chemical analysis slide 5 by a new chemical analysis slide 5 on which the sample solution has not yet been applied which is being fed into the chamber 2. Therefore, ejection of the chemical analysis slide 5 for which the optical measurement has already been finished can be effected simultaneously with feeding of the new chemical analysis slide 5 into the chamber 2, and background measurement and sample application can be carried out immediately the new chemical analysis slide 5 has been fed into the chamber 2. Consequently, these operations can be completed within, for example, approximately four seconds, i.e. within the slide feed-in time of approximately two seconds plus the sample application time of approximately two seconds (background measurement is completed instantaneously). The rate measurement for the chemical analysis slides 5, 5, . . . in the other chambers 2, 2, . . . may be carried out within the remaining time of approximately six seconds. Thus, the aforesaid embodiment can substantially satisfy the aforesaid requirements.

If slide feeding and slide ejection are carried out independently unlike in the present invention, the time required for the operations increases. Also, in the case where the sample application means 8 and the probe 9 are not disposed on the straight line 1, for example, it is necessary to rotate the chamber 2 after the chemical analysis slide 5 is fed thereinto up to the position at which the probe 9 is present, to carry out background measurement, then to rotate the chamber 2 up to the position at which the sample application means 8 is present, and to apply the sample solution to the chemical analysis slide 5 housed in the chamber 2. In this case, a long time is required for slide feeding, slide ejection, background measurement, and sample application, and the aforesaid requirements cannot always be substantially satisfied.

The configuration in accordance with the present invention is applicable also to chemical analysis apparatuses using a measurement method differing from the measurement method in which background measurement and rate measurement are carried out. Also, the incubator may be shaped in a form other than the circular form insofar as the chambers are located on the same circumference. Further, the slide feed means 11 and the slide ejection unit 12 may be disposed respectively outward and inward of the circumference A with the predetermined position P intervening therebetween.

I claim:
1. A chemical analysis apparatus comprising:
  i) an incubator provided with a plurality of chambers disposed on the same circumference for each housing a chemical analysis slide, said incubator also having a plurality of sample application openings and a plurality of measurement openings therein.
  ii) a sample application means disposed above said incubator at a predetermined position on said circumference, and a probe disposed below said incubator at said predetermined position.

iii) a rotation means for rotating said incubator to locate said chambers one after another at said predetermined position, and iv) a slide feed means disposed outward or inward of said circumference to face said predetermined position, and a slide ejection unit disposed on the side opposite to said slide feed means with said predetermined position intervening between said slide ejection unit and said slide feed means.

wherein said chemical analysis slide in each of said chambers is pushed out and ejected by feeding of a new chemical analysis slide into said chamber.

2. An apparatus as defined in claim 1, wherein said incubator is formed in a doughnut shape, and said chambers are disposed in an equally spaced relation to each other on the same circumference of said doughnut-shaped incubator.

3. An apparatus as defined in claim 1, wherein said slide feed means comprises a feed unit for housing therein a plurality of said chemical analysis slides stacked one upon another, and a pushing lever for pushing the lowest chemical analysis slide in said feed unit out of said feed unit into said chamber via a lever inlet opening and a slide outlet opening formed at lower portions of said walls of said feed unit.

4. An apparatus as defined in claim 1, wherein each said sample application opening has an outer end, which opens at an upper surface of said incubator, and an inner end which opens at an upper portion of a corresponding one of said chambers, and further wherein each said measurement opening has an outer end, which opens at a lower surface of said incubator, and an inner end which opens at a lower portion of a corresponding one of said chambers, so that said sample application opening and said measurement opening face a multi-layer film of said chemical analysis slide when said chemical analysis slide is housed in each of said chambers.

5. An apparatus as defined in claim 1, wherein said slide feed means and said slide ejection unit are disposed on a straight line which includes said predetermined position.

* * * * *